United States Patent [19]

Mohrin

[11] Patent Number: 5,389,747
[45] Date of Patent: Feb. 14, 1995

[54] STETHOSCOPE

[76] Inventor: Carl M. Mohrin, 186 Charlestown Rd. R.R. #3, Hampton, N.J. 08827

[21] Appl. No.: 106,825

[22] Filed: Aug. 16, 1993

[51] Int. Cl.$^6$ ............................................. A61B 7/02
[52] U.S. Cl. ................................. 181/131; 181/137
[58] Field of Search .................... 181/131, 137; 381/67

[56] References Cited

U.S. PATENT DOCUMENTS

| | | | |
|---|---|---|---|
| 2,414,850 | 1/1947 | Brandenburg | 181/131 |
| 3,193,047 | 7/1965 | Allen | 181/131 |
| 3,223,195 | 12/1965 | Allen | 181/131 |
| 3,302,747 | 2/1967 | Taeschler | 181/131 |
| 3,601,218 | 3/1970 | Reynolds, Jr. | 181/131 |
| 3,690,404 | 9/1972 | Collins | 181/131 |
| 3,951,230 | 4/1976 | Littmann | 181/131 |
| 4,027,116 | 5/1977 | Nakamura | 181/131 |
| 4,239,089 | 12/1980 | Nelson | 181/131 |
| 4,270,627 | 6/1981 | Hill | 181/131 |
| 4,669,572 | 6/1987 | Fassbender | 181/137 |
| 4,995,473 | 2/1991 | Packard | 181/137 |
| 5,022,487 | 6/1991 | Kirchner | 181/137 |

FOREIGN PATENT DOCUMENTS 0379010  7/1990  European Pat. Off. .

OTHER PUBLICATIONS

Gardner D. Hiscox, "Mechanical Movements", 1903; p. 389, Publ. in New York by Norman Henley and Co.

*Primary Examiner*—Howard B. Blankenship
*Assistant Examiner*—Eddie C. Lee
*Attorney, Agent, or Firm*—Adel A. Ahmed

[57] ABSTRACT

A stethoscope head comprises a bell housing, for resonating, a diaphragm arrangement for sound communication, and a user operable selector control for selectively providing an opening in the diaphragm.

22 Claims, 5 Drawing Sheets

STETHOSCOPE

The present invention relates generally to stethoscopes and, more particularly, to stethoscopes exhibiting selectable frequency response characteristics.

Auscultation is a term in medicine applied to a method employed by physicians for determining, by the sense of hearing, the condition of certain internal organs. Until the introduction of the stethoscope, early physicians practiced auscultation by applying the ear to, for example, the region over the heart. A stethoscope is an instrument used for listening to sounds produced by the action of the lungs, heart, and other internal organs. In 1819, the stethoscope in the form of a flanged tube was invented by the French physician, René La̋ennec (1781–1826). The American physician, George Cammann (1804–63) invented the well-known binaural stethoscope, which is the type now generally used. This typically comprises a small sound-chamber acoustically coupled to two flexible sound tubes fitted with earpieces. The sound-chamber is variously referred to as the stethoscope head, chest-piece, the receiving head or bell, and in some cases is in the form of a small drum or diaphragm box.

The most generally used sound-chambers are the "open" or "bell-type" and the "diaphragm" type. The bell type comprises a generally bell-shaped cavity whose open end is applied to the patient and whose other end is coupled to the sound tubes. It is better suited for listening for low-pitched heart sounds such as presystolic and certain systolic murmurs, gallop rhythms and certain other heart sounds. The diaphragm type head comprises a sound chamber closed off by a flexible diaphragm which is applied to the patient. It is better suited for listening for higher pitched or higher frequency sounds. Thus, the frequency response is spectrally different for the two types, each tending to emphasize preferentially a different frequency range or ranges of sound.

For proper diagnosis it is desirable that the physician be able to change the head from a bell type of sound-chamber to a diaphragm type of sound-chamber. Various stethoscopes have been introduced which permit changing the head from a bell type of sound-chamber to diaphragm type of sound-chamber to accommodate this need or, as sometimes stated, for changing the frequency response characteristic.

For examples of the foregoing, and for examples of stethoscopes intended to provide various forms of frequency selective and other desirable characteristics, see e.g. U.S. Pat. No. 5,022,487, issued Jun. 11, 1991 in the name of Kirchner; U.S. Pat. No. 4,995,473 issued Feb. 26, 1991 in the name of Packard; U.S. Pat. No. 4,669,572 issued Jun. 2, 1987 in the name of Fassbender; U.S. Pat. No. 4,270,627 issued Jun. 2, 1981 in the name of Hill; U.S. Pat. No. 4,239,089 issued Dec. 16, 1980 in the name of Nelson; U.S. Pat. No. 3,951,230 issued Apr. 20, 1976 in the name of Littmann; U.S. Pat. No. 3,690,404, issued Sep. 12, 1972 in the name of Collins; U.S. Pat. No. 3,302,747 issued Feb. 7, 1967 in the name of Taeschler; and U.S. Pat. No. 2,414,850 issued Jan. 28, 1947 in the name of Brandenburg.

However, in many cases, this change-over requires the head to be removed from a patient for the change to be effected. It is herein recognized that such removal of the stethoscope head from the patient for changing the sound-chamber is undesirable for the reason that the physician may have found a critical location where it would now be desirable to listen to the sounds at that location but through another sound-chamber. Following removal of stethoscope head and switching over to another sound-chamber, replacement of the stethoscope head may not take place in precisely the same location on the patient. Thus, it is important that the sound at one and the same location be listened to by the physician through the different heads and a comparison made. Such comparison also involves comparing the impression left by one set of sounds with another set of sounds and it has been recognized in the art that, to that end, it is undesirable to interpose a delay occasioned by the removal of the stethoscope head, its readjustment, and subsequent replacement and then possibly having to spend further time searching for the previous location which cannot now anyway be recognized by listening for the sounds as heard through the previously used head.

The afore-mentioned U.S. Pat. Nos. 5,022,487 (Kirchner) and 4,669,572 (Fassbender) disclose rotatable members for altering the frequency response and 3,690,404 (Collins) discloses rotatable members for altering the frequency response in situ. The afore-mentioned U.S. Pat. No. 3,951,230 (Littmann) discloses a stethoscope head wherein a diaphragm sound chamber is disposed within a housing which allows for the head to be used as a diaphragm sound chamber or a bell sound chamber without removal of the stethoscope head from the patient. The above-mentioned stethoscope heads utilize a considerable number of parts. As described, the Littmann head allows the selection without the need for removal from the patient, of one or the other of the diaphragm sound chamber or bell sound chamber.

In accordance with an aspect of the invention, a stethoscope head comprises a bell housing for resonating, a diaphragm arrangement for sound communication, and a user operable selector control for selectively providing an opening in the diaphragm.

In accordance with another aspect of the invention, a stethoscope head comprises a bell housing having a mouth end; a first diaphragm, having a respective opening therein, and being coupled to the bell housing at the mouth end; and a second diaphragm, having a respective opening therein, and being rotatably coupled to the bell housing in juxtaposition to the first diaphragm.

In accordance with another aspect of the invention, the second diaphragm is rotatable to a first position wherein the respective opening in the first diaphragm is in alignment with the respective opening in the second diaphragm.

In accordance with another aspect of the invention, the second diaphragm is rotatable to a second position wherein the respective openings in the first and second diaphragms are substantially completely out of alignment.

In accordance with another aspect of the invention, the second diaphragm is rotatable to a third position wherein the respective openings in the first and second diaphragms are in partial alignment.

In accordance with another aspect of the invention, the bell housing has a tubing nipple formed thereon for receiving a sound communicating tube.

In accordance with another aspect of the invention, a stethoscope head includes a sound communicating tube coupled at one end thereof to the tubing nipple and coupled at another end thereof to earpieces.

In accordance with still another aspect of the invention, a stethoscope head comprises a bell housing arrangement for resonating; a diaphragm arrangement for sound communication; and a user operable selection arrangement for selectively providing an opening in the diaphragm arrangement.

In accordance with still another aspect of the invention, the user operable selection arrangement is operable with the stethoscope head in situ on a patient during an auscultation procedure.

In accordance with yet another aspect of the invention, a stethoscope head comprises a bell housing having a mouth end; a diaphragm attached across the mouth end; and the diaphragm comprises a disk valve.

In accordance with yet another aspect of the invention, the diaphragm has an opening formed therein; and the disk valve comprises a further diaphragm having an opening formed therein.

In accordance with yet another aspect of the invention, the diaphragm has a plurality of openings therein; and the further diaphragm has a further plurality of openings therein corresponding to the openings in the diaphragm.

In accordance with still yet another aspect of the invention, a stethoscope head comprises a bell housing having a mouth; a composite diaphragm attached across the mouth, wherein the diaphragm comprises first and second diaphragms being in juxtaposition and adapted for relative rotation for selectively bringing into and out of alignment respective openings or holes in the first and second diaphragm such that when the holes are out of alignment, the composite diaphragm causes the stethoscope head to function as a diaphragm head and when the openings or holes are in alignment, the composite diaphragm causes the stethoscope head to function as a bell head.

In accordance with a further aspect of the invention, a stethoscope head comprises a bell housing; and a disk valve coupled to the bell housing for providing continuous variation of acoustic response between, at one extreme, a bell type of response characteristic and, at another extreme, a diaphragm type of response characteristic.

In accordance with still a further aspect of the invention, a method of in situ bell and diaphragm response auscultation with a stethoscope head having a fixed diaphragm with perforations and a rotatable diaphragm with perforations, comprises the steps of:

(a) selecting a position of the rotatable diaphragm so as to bring into alignment the perforations in the fixed and rotatable diaphragms;

(b) applying the stethoscope head to a patient for auscultation:

(c) with the stethoscope head still applied to the patient, selecting a position of the rotatable diaphragm so as to bring out of alignment the perforations in the fixed and rotatable diaphragms; and (d) continuing auscultation of the patient.

For the detailed description of preferred embodiments of the invention which follows, reference is made to the drawing in which FIG. 1 shows a partly sectioned and partly outside side elevation view of a stethoscope head in accordance with the present invention, not necessarily to scale;

Figure 1:
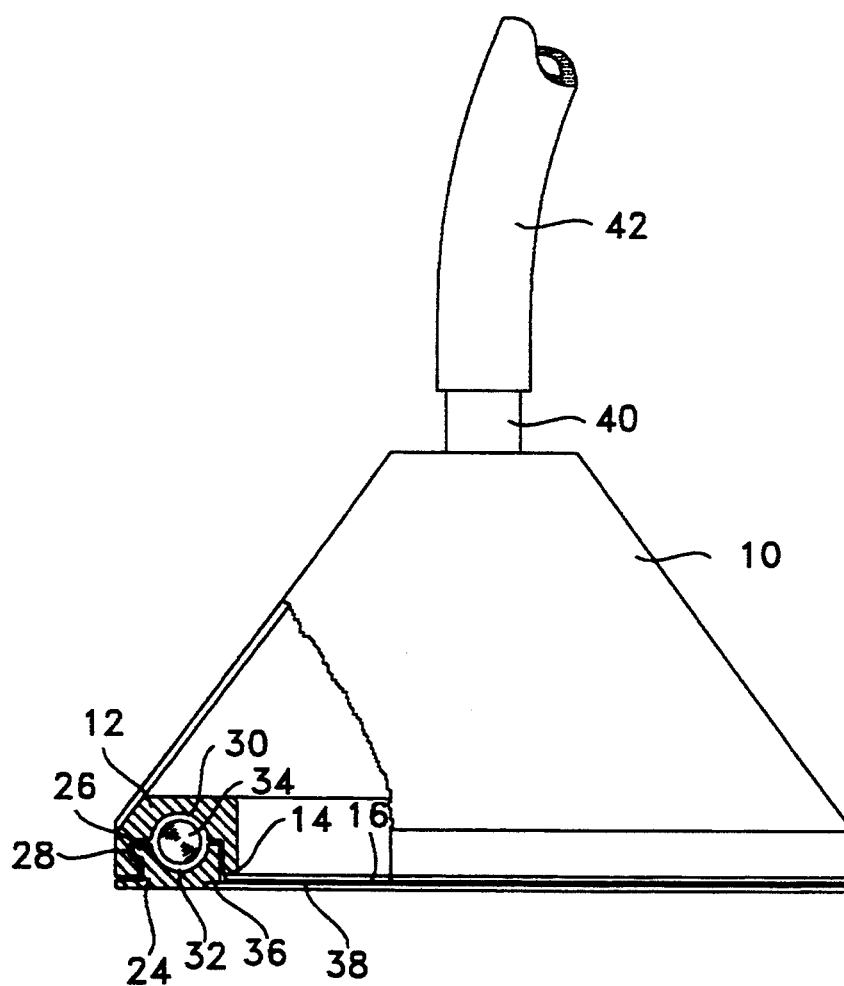
Figure 2:
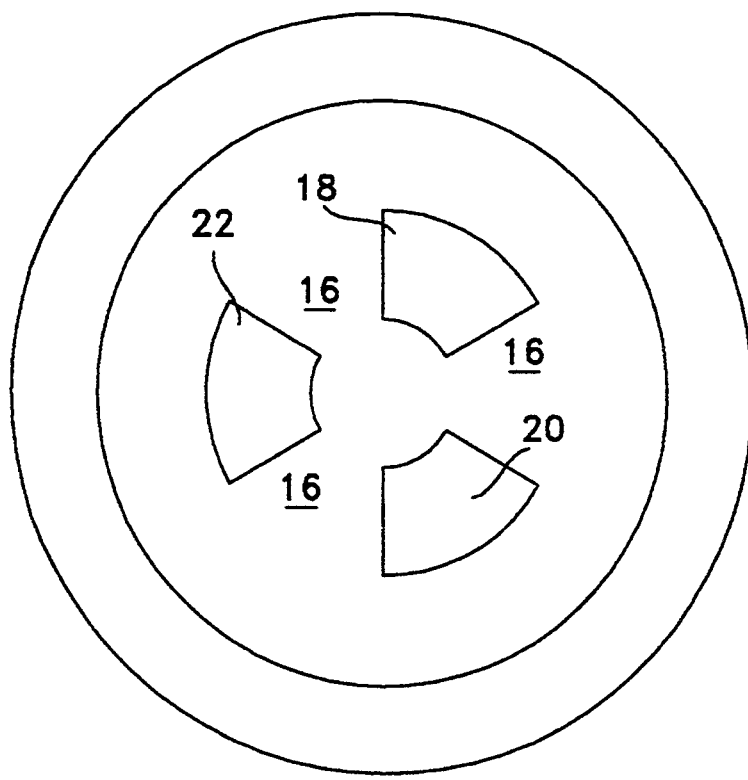
FIG. 2 is a bottom plan view of the embodiment of FIG. 1, drawn in third angle projection relative to FIG. 1, and not necessarily to scale.
Figure 3:
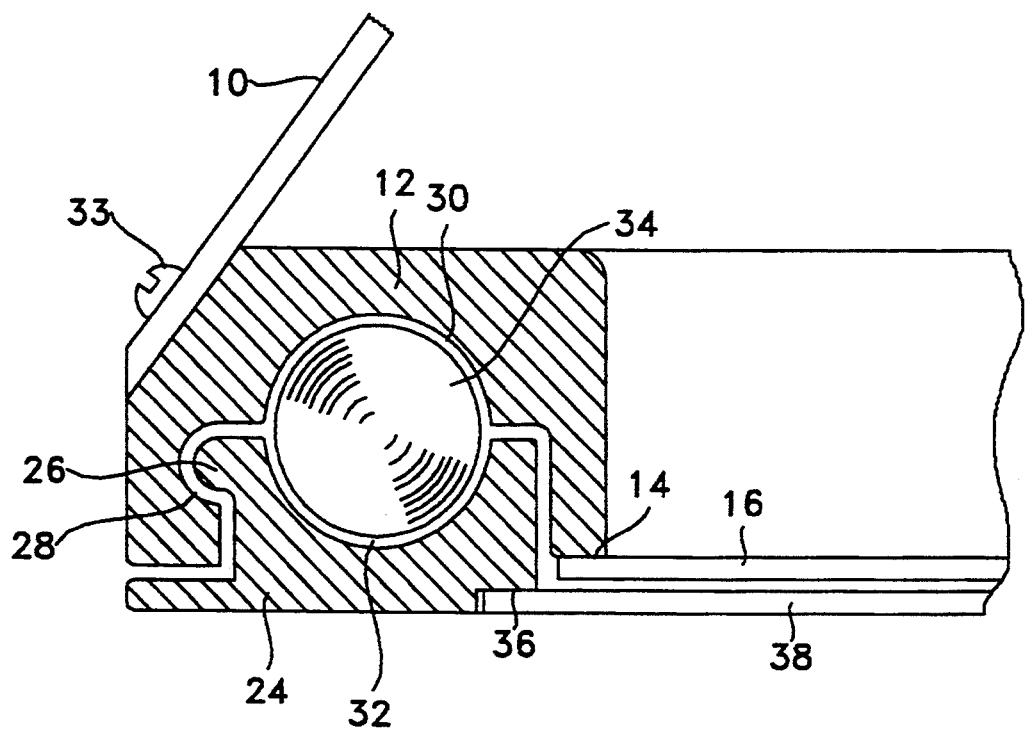
FIG. 3 shows a portion of the embodiment of FIG. 1, drawn to a larger scale, but not necessarily to scale, as a help to gaining a clearer understanding of details of the invention.

In FIG. 1, see also FIGS. 2 and 3, a bell housing 10 is attached at its "mouth" end to a first bearing ring 12. Attached to an annular surface 14 formed on the bottom surface of first bearing ring 12 is a first diaphragm 16, substantially flat and extending across the whole inside cross-section of bearing ring 12, defined by annular surface 14. Thus, diaphragm 16 is substantially circular. Diaphragm 16 has formed therein three openings or perforations, 18, 20, and 22, each occupying a respective angular sector of about 60 degrees of arc and being spaced from its neighboring openings by an angular sector of diaphragm 16 of about sixty degrees of arc. The sides of openings 18, 20, and 22 are substantially straight, running along respective radii from the center of diaphragm 16. The inner and outer edges of openings 18, 20, and 22 are arcuate, running substantially along a circumference of a respective circle centered at the center of diaphragm 16. The inner and outer edges are of openings 18, 20, and 22 are respectively near the center and periphery of diaphragm 16, with sufficient separation therefrom such that diaphragm 16 is not substantially weakened by the presence of the openings. Thus, the length of openings 18, 20, and 22 may each occupy 50–80 percent of the radius of diaphragm 16, or thereabouts.

A second bearing ring 24 has formed thereon an annular protrusion 26 for cooperatively engaging an annular slot 28 formed in bearing ring 12 such that bearing ring 24 is captive to 12 and is free to rotate relative thereto. Each of bearing ring 12 and bearing ring 24 has formed therein an annular channel of approximately semicircular cross-section, respectively designated as 30 and 32. The open ends of channels 30 and 32 are juxtaposed so that almost a full circle is thereby formed. Bearing balls, of which only one representative ball, 34, is shown in FIG. 1, are contained in channels 30 and 32 which thus form a ball bearing race for relative movement between bearing rings 12 and 24. FIG. 3 shows the same arrangement in larger format for greater clarity, where like parts are indicated by the same reference numerals. Additionally, the embodiment of FIG. 3 shows a screw 33 attaching bell housing 10 to bearing ring 12.

Bearing ring 24 has formed on the under surface thereof an annular surface 36. A second diaphragm 38 is attached to annular surface 36; diaphragm 38 is substantially flat and extends across the whole inside cross-section of bearing ring 24, defined by annular surface 36. Thus diaphragm 38 is substantially circular. Diaphragm 38 has formed therein 3 openings 18', 20', and 22', substantially the same shape and size as openings 18, 20, and 22 formed in diaphragm 16. Annular surfaces 14 and 36 are so arranged dimensionally that the bottom surface of diaphragm 16 and the upper surface of diaphragm 38 are either touching or in are in very close proximity.

Figure 4A:
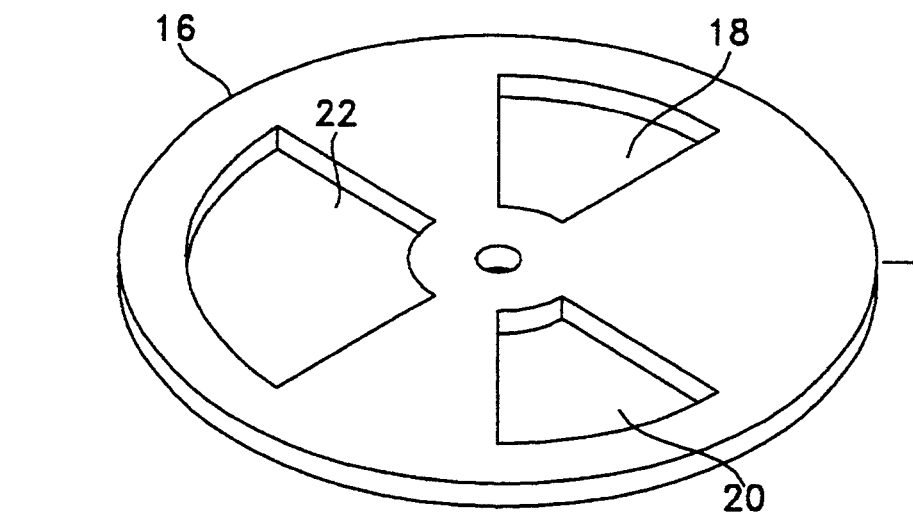
FIGS. 4A and 4B show portions of the FIG. 1 embodiment drawn in approximate accordance with the principles of isometric projection, not necessarily to scale.
Figure 4A:
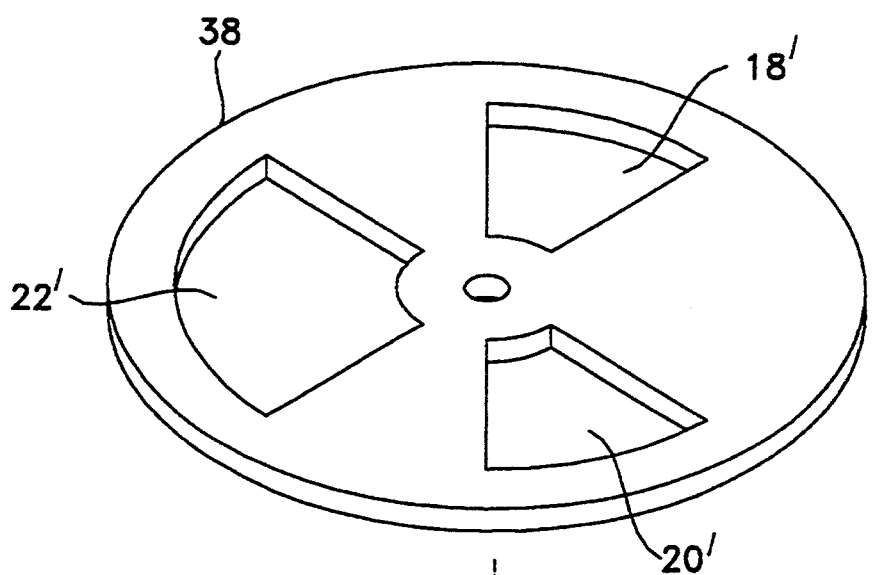

FIG. 4A shows isometric diagrammatic form diaphragms 16' and 38' with their respective openings. Diaphragms 16' and 38' additionally each have a central hole for receiving a small rivet 37, of metal or of plastic, for added stability in the event the diaphragm material requires it.

Figure 4B:
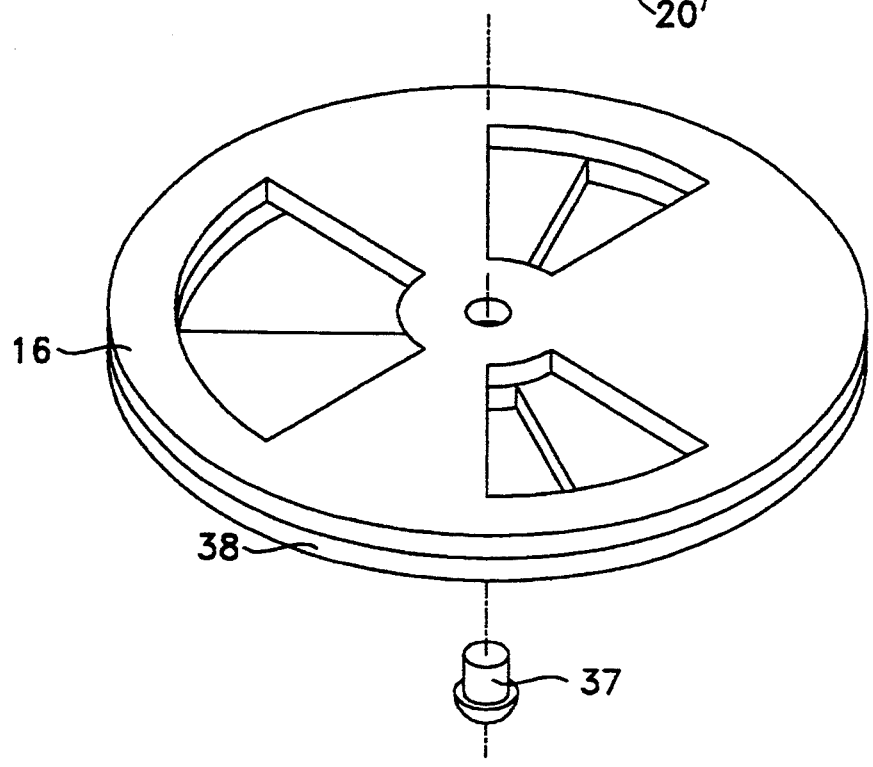

In FIG. 4B, the diaphragms are shown in their juxtaposed situation. The diaphragms thus function as a form of "disk valve" comprising two disks so that the size of the through openings can be varied by relative rotation of the diaphragms from a fully open position, where the respective openings in the two diaphragms are in full or complete registration or alignment, that is, the openings coincide fully so as to form a through opening of the same shape as the respective openings, and where the through openings are the same as the openings on each diaphragm, to a fully closed position where the respective openings in each diaphragm are completely out of registration or alignment with those on the other diaphragm so that the through opening is zero. Disk valves, such as for controlling fluid flow, are known in the art. See, for example, "Mechanical Movements," by Gardner D. Hiscox, publ. Norman Henley and Co., New York, 1903; page 389. In the FIG. 3B embodiment, the diaphragms are shown in a position of relative rotation of about 40 degrees away from a fully open position.

Figure 5:
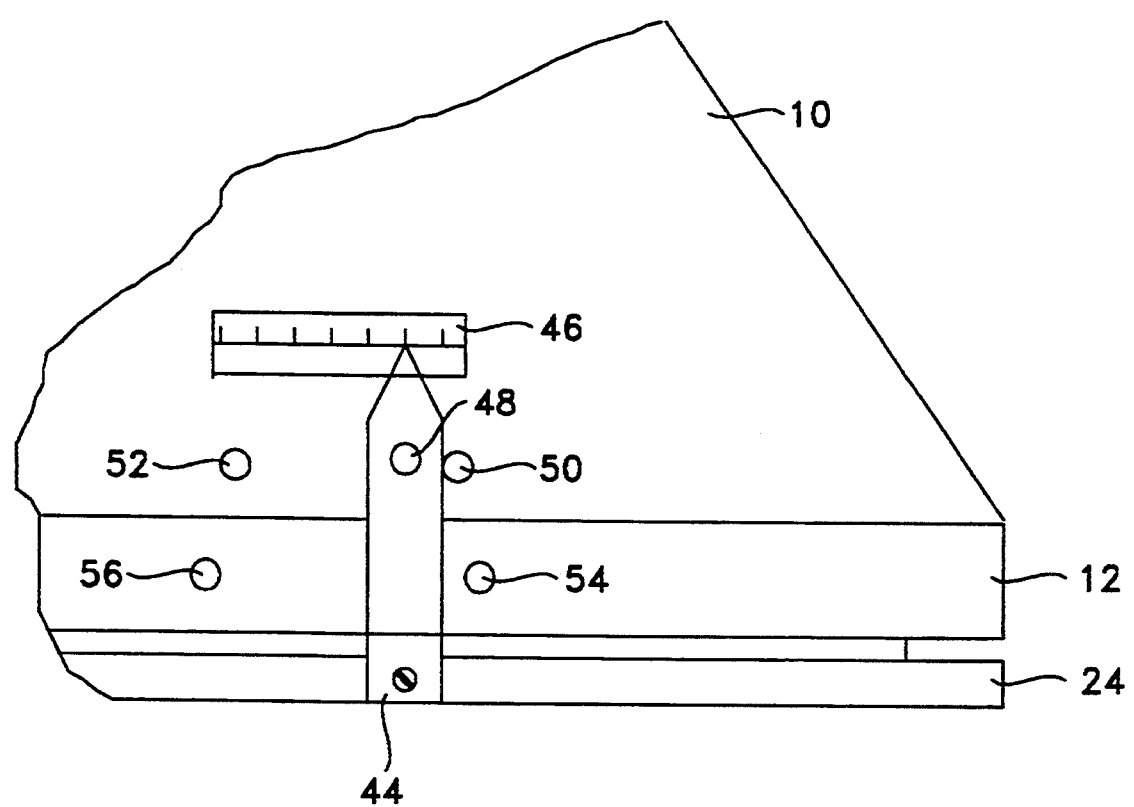
FIG. 5 shows a further embodiment.

In the FIG. 5 embodiment, and index arm 44 is attached to bearing 24, serving as pointer to indicate on a scale 46 the position of bearing ring 24 relative to bell housing 10. In that bell housing 10 is attached to bearing ring 12, index arm 40 thus indicates the relative rotational position of bearing rings 12 and 24. Index arm 44 is formed in a springy manner so as to press lightly against bell housing 10, and has a "dimple" 48 formed thereon which is arranged for selective cooperative engagement with small depressions or "dimples" 50 and 52 formed in the surface of bell housing 10, so as to provide a moderate detent action, as will explained below in the operation of the stethoscope. Limit pins 54 and 56 are provided in one embodiment so as to limit the movement of index arm 40 and so to limit the extent of possible relative rotation of bearing rings 12 and 24.

Figure 6:
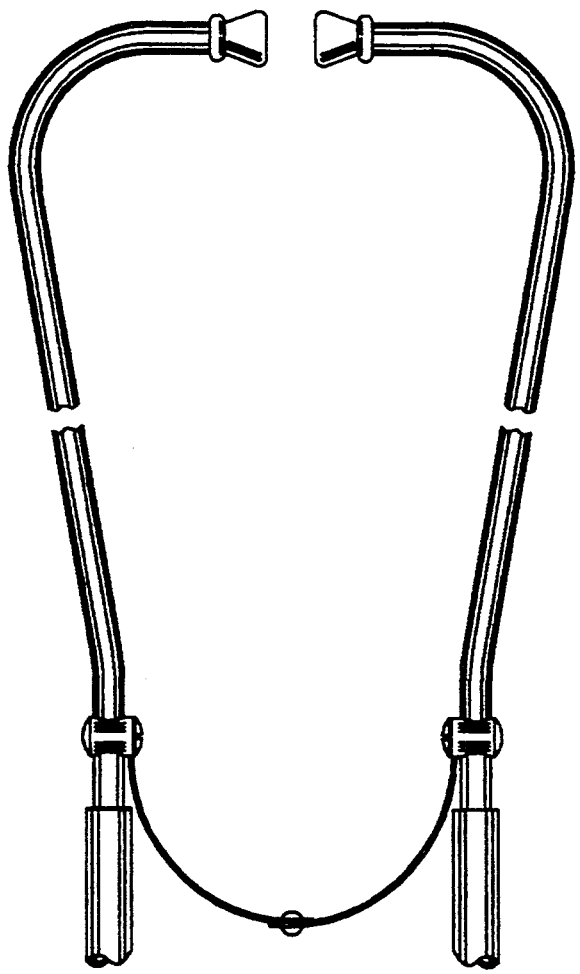
FIG. 6 shows a stethoscope in accordance with the invention.
Figure 6:
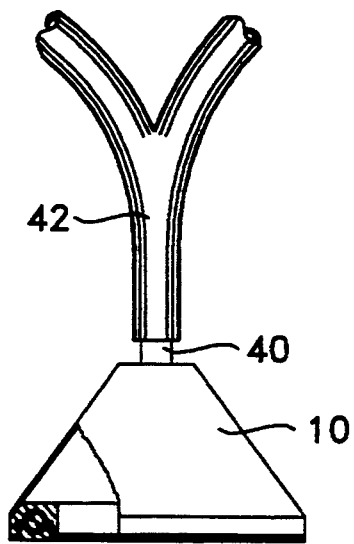

At the top of bell housing 10 and in acoustic communication with the chamber formed by bell housing 10 is a nipple 40, having an annular tube-retaining protrusion or tubing nipple, for coupling in a known manner to a rubber or plastic tube 42. As shown in FIG. 6, tube 42 is coupled by a Y connector to spring-loaded adapted for a user's ears.

In operation, the bottom of the stethoscope head, corresponding approximately to the plane of diaphragm 38 and the bottom surface of bearing ring 24, is placed against the patient's body for auscultation. Because of the low friction rotational mutual coupling of bearing rings 12 and 24, bearing ring 12 is easily rotatable by hand relative to bearing ring 24, by grasping turning bell housing 10 with the fingers and twisting it. There is no special need to holding bearing ring 24 still during this process since it is kept stationary by friction with the patient's body. In a first position, bearing rings 12 and 24 are in such relationship that openings 18, 20, and 22 are aligned with the areas between openings 18', 20', and 22' so that diaphragms 16 and 38 form a combination having no through opening. Acoustically, the combination of diaphragms 16 and 38 operate as one composite diaphragm and the response characteristic of the stethoscope in accordance with the invention corresponds to the "diaphragm" response of a conventional diaphragm stethoscope.

In a second relative position, openings 18, 20, and 22 are aligned with openings 18', 20', and 22' so that diaphragms 16 and 38 form a combination having clear openings therethrough for the passage of sound. Under this condition, the composite diaphragm formed by the combination of diaphragms 16 and 38 has negligible effect on the response characteristic of the stethoscope which will now exhibit a "bell" type of response corresponding to a conventional bell stethoscope. It is noted that the changeover is effected without having to remove the stethoscope from the patient, so that the patient body point of auscultation remains the same. Furthermore, an immediate comparing and contrasting of the sounds under both options is possible, the physician being able to change back and forth between modes at pleasure by a mere twist of the stethoscope head.

The positions of detent dimples 46 and 48 can be selected to correspond with the first and second relative positions, respectively, so that the physician need not look at any marking but can simply tell by feel and habit which type of response characteristic is being used by simply selecting "full right" or "full left" rotation, for example.

While the "diaphragm" and "bell" type of response characteristics represent traditional and familiar points of reference, other useful types of sound data can be obtained with the stethoscope in accordance with the present invention. Thus, by selecting positions intermediate the fully open and fully closed positions, other response characteristics can be obtained which are in between the diaphragm and bell response characteristics. Such flexibility allows the physician to focus on unusual symptoms where, for example, a weak sound signal of interest may be submerged in a louder background of different sounds. The weak sound signal may have a quite different spectral energy distribution as compared with the background interfering sounds and yet it may be masked because of its weak amplitude. By selecting a particular response characteristic so as to exploit the different frequency spectra involved, it is possible in some circumstances to enhance the sound of interest while attenuating the background. The ease with which this is accomplished in the present invention makes this type of "fine tuning" practicable. Scale 42 with index arm and pointer 40 can serve to note a scale reading corresponding to a response which has proven particularly helpful.

FIG. 6 shows in diagrammatic form a stethoscope with a head in accordance with an embodiment of the invention.

The invention has been described by way of exemplary embodiments. It will be apparent that various modifications and changes can be made without departing from the spirit of the invention. The construction is of great simplicity with few parts or assembly operations being needed; clearly, fabrication details and materials used can be varied so that parts may be glued, screwed, or rivetted together, depending on the materials used and for convenience in mass production. Furthermore, the particular ball bearing arrangement shown allowing mutual rotation of bearing rings 12 and 24 can be replaced by a number of other possible arrangements. For example, a simple friction bearing arrangement can be satisfactory, preferably using low friction plastic materials. The actual shape of bell housing 10 and of bearing rings 12 and 24, as well as the attachment of diaphragms 16 and 38 can be varied considerably while continuing to provide satisfactory operation. The shape and number of the openings 18, 20, and 22 and the corresponding openings 18', 20', and 22' can be made quite different from the sectorial holes used in the described exemplary embodiment. For example, round holes can be readily envisioned, or indeed, just one hole in each diaphragm. These and like changes are contemplated to be part of the invention, which is defined by the claims following.

I claim:

1. A stethoscope head comprising:
   a bell housing having a mouth end;
   a first diaphragm, having a respective opening therein, and being coupled to said bell housing at said mouth end; and
   a second diaphragm, having a respective opening therein, and being rotatably coupled to said bell housing in juxtaposition to said first diaphragm, said first and second diaphragms forming a composite diaphragm adapted for placement against a patient's body for auscultation.

2. A stethoscope head in accordance with claim 1 wherein said second diaphragm is rotatable to a first position wherein said respective opening in said first diaphragm is in alignment with said respective opening in said second diaphragm.

3. A stethoscope head in accordance with claim 1 wherein said second diaphragm is rotatable to a second position wherein said respective openings in said first and second diaphragms are substantially completely out of alignment.

4. A stethoscope head in accordance with claim 1 wherein said second diaphragm is rotatable to a third position wherein said respective openings in said first and second diaphragms are in partial alignment.

5. A stethoscope head in accordance with claim 1 wherein said bell housing has a tubing nipple formed thereon for receiving a sound communicating tube.

6. A stethoscope head in accordance with claim 1 including a sound communicating tube coupled at one end thereof to said tubing nipple and coupled at another end thereof to earpieces.

7. A stethoscope head, comprising:
   bell housing means for resonating;
   composite diaphragm means, comprising first and second juxtaposed diaphragms, said composite diaphragm being coupled to said bell housing means for sound communication; and
   user operable selection means, coupled to said diaphragm means for selectively providing an opening in said composite diaphragm means.

8. A stethoscope head in accordance with claim 7 wherein said user operable selection means is operable with said stethoscope head in situ on a patient during an auscultation procedure.

9. A stethoscope head comprising:
   a bell housing having a mouth end;
   a composite diaphragm attached across said mouth end; and
   said composite diaphragm comprising a first acoustically responsive diaphragm and a further acoustically responsive diaphragm for forming in combination with said first acoustically responsive diaphragm a disk valve.

10. A stethoscope head in accordance with claim 9 wherein
    said first acoustically responsive diaphragm has an opening formed therein; and
    said disk valve comprises said further acoustically responsive diaphragm having an opening formed therein.

11. A stethoscope head in accordance with claim 10 wherein
    said first acoustically responsive diaphragm has a plurality of openings therein; and
    said further acoustically responsive diaphragm has a further plurality of openings therein corresponding said openings in said diaphragm.

12. A stethoscope head in accordance with claim 11 including means for providing relative rotation of said first acoustically responsive diaphragm and said further acoustically responsive diaphragm such that said plurality of openings and said further plurality of openings can be selectively brought into alignment and out of alignment.

13. A stethoscope head in accordance with claim 12 wherein
    said first acoustically responsive diaphragm and said acoustically responsive further diaphragm are in close proximity so as to function substantially as a single diaphragm when said pluralities of openings are out of alignment.

14. A stethoscope head comprising:
    a bell housing;
    a first bearing ring coupled to said bell housing;
    a first diaphragm attached to said first bearing ring;
    a second bearing ring rotatably coupled to said first bearing ring;
    a second diaphragm attached to said second bearing ring; and
    said first and second diaphragms having therein respective openings such that when said first and second diaphragms are in a first angular relationship said respective openings are in alignment and when said first and second diaphragms are in a second angular relationship said respective openings are out of alignment such that said first and second diaphragms function cooperatively as one composite acoustical diaphragm.

15. A stethoscope head in accordance with claim 14, wherein when said respective openings are in alignment, direct communication by air waves for sound is established between a patient sound source and said bell housing, and when said respective openings are out of alignment, no direct communication by air waves for sound is established between a patient sound source and said bell housing.

16. A stethoscope head in accordance with claim 14, wherein said first and second bearing rings are coupled by ball bearings.

17. A stethoscope head comprising:
    a bell housing having a mouth;
    a composite diaphragm attached across said mouth, wherein said diaphragm comprises first and second diaphragms being in juxtaposition and adapted for relative rotation for selectively bringing into and out of alignment respective openings or holes in said first and second diaphragm such that when said holes are out of alignment, said composite diaphragm causes said stethoscope head to function as a diaphragm head with said composite diaphragm forming the effective diaphragm thereof and when said openings or holes are in alignment, said composite diaphragm causes said stethoscope head to function as a bell head.

18. A stethoscope head comprising:
a bell housing; and
a disk valve having user selectable opening size and being coupled to said bell housing for providing continuous variation of acoustic response between a bell type of response characteristic and a diaphragm type of response characteristic, said disk valve being adapted for operation as a composite acoustic diaphragm.

19. A stethoscope head in accordance with claim 18, wherein said disk valve comprises first and second disks in closely proximate planes, said first disk having formed therein a first plurality of openings and said second disk having therein a second plurality of openings, said first and second pluralities of openings being arranged to come into alignment for providing clear passages through said first and second disks, corresponding to said openings, at a first relative rotational position between said first and second disks.

20. A stethoscope head in accordance with claim 19, wherein said first and second pluralities of openings are arranged to be out of alignment for providing no passages through said first and second disks, at a second relative rotational position between said first and second disks.

21. A method of in situ bell and diaphragm response auscultation with a stethoscope head having a composite diaphragm comprising a fixed diaphragm with perforations and a rotatable diaphragm with perforations, said fixed and rotatable diaphragms being in close juxtaposition so as to be capable of operating acoustically substantially as a single composite diaphragm, comprising the steps of:
(a) selecting a position of said rotatable diaphragm so as to bring into alignment said perforations in said fixed and rotatable diaphragms;
(b) applying said composite diaphragm of said stethoscope head to a patient for auscultation:
(c) with said stethoscope head still applied to said patient, selecting a position of said rotatable diaphragm so as to bring out of alignment said perforations in said fixed and rotatable diaphragms; and
(d) continuing auscultation of said patient.

22. A method of in situ auscultation in accordance with claim 21 wherein positions of said rotatable diaphragm in steps (a) and (c) are interchanged.

* * * * *